Figure 1:
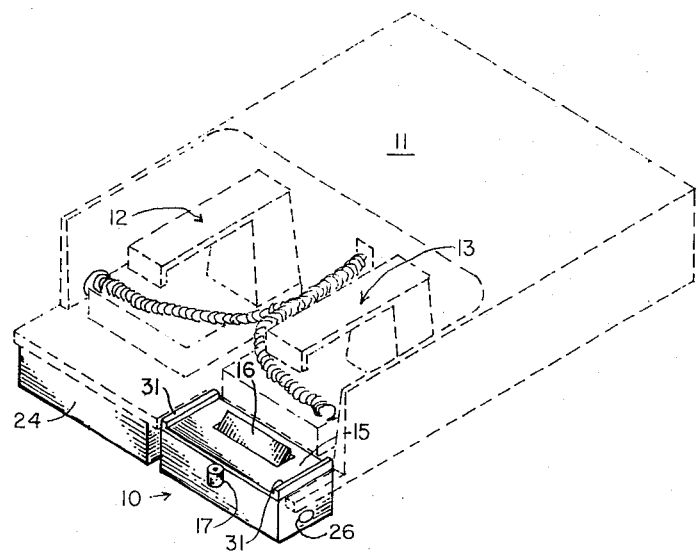

United States Patent [19]

Washburn

[11] Patent Number: 4,464,412

[45] Date of Patent: Aug. 7, 1984

[54] DEFIBRILLATOR GEL DISPENSER

[76] Inventor: Jack S. Washburn, 1414 Sunset Ave. Extension, Asheboro, N.C. 27203

[21] Appl. No.: 435,674

[22] Filed: Oct. 21, 1982

[51] Int. Cl.³ .................... G01R 27/02; A61B 5/04; A01N 1/02

[52] U.S. Cl. .................................. 427/2; 128/419 D; 128/639; 128/803; 324/65 R

[58] Field of Search .................. 141/360, 361, 362; 128/419 D, 639, 803; 427/2; 324/65 R

[56] References Cited

U.S. PATENT DOCUMENTS

| D. 252,821 | 9/1979 | Moore et al. | 24/29 D |
|---|---|---|---|
| 1,942,556 | 1/1934 | Kirk | 221/102 |
| 2,411,923 | 12/1946 | Kotraba | 222/127 |
| 2,634,026 | 4/1953 | Yuan | 222/127 |
| 2,775,989 | 1/1957 | Jensen | 141/360 |
| 3,020,941 | 2/1962 | Corley | 141/360 |
| 3,467,863 | 9/1969 | Karsh | 128/419 D X |
| 3,942,533 | 3/1976 | Cannon | 128/803 X |
| 4,058,127 | 11/1977 | Buchalter | 128/419 D X |

OTHER PUBLICATIONS

Brochure entitled: *Lifepak 5-Operating Instructions;* no date available (Physio-Control).
*Defibrillation-What You Should Know* Brochure by Sandra Higgins, Copyright 1978, (Physio-Control).

*Primary Examiner*—Michael R. Lusignan

[57] ABSTRACT

The invention as presented herein demonstrates an apparatus and method whereby gel can be quickly and easily dispensed onto the contact surface of a defibrillator paddle. The dispenser allows the user to maintain his grip on the paddles while applying the gel thus preventing the paddles from coming into contact with unclean surfaces prior to defibrillation while providing convenience to the user.

9 Claims, 6 Drawing Figures

U.S. Patent   Aug. 7, 1984   4,464,412

DEFIBRILLATOR GEL DISPENSER

BACKGROUND AND OBJECTIVES OF THE INVENTION

As is well known, defibrillation comprises delivering an electric charge through the heart of a patient to terminate the potentially fatal arrhythmia, ventricular fibrillation. Ventricular fibrillation may occur with ordinary disease, myocardial infarction, drownings, acid-base disturbances, electric shock or can be associated with other life threatening situations. By the use of paddle electrodes, electrical energy can be delivered through the heart in short controlled bursts which will stop fibrillation which is often characterized by electrical and mechanical chaos.

Defibrillation is generally carried out by the use of two paddle electrodes which are placed on the patient's chest and the current passes from one electrode through the patient's heart to the second electrode. Defibrillator paddles generally have a handle and a contact surface which may vary in size. Both adult and smaller pediatric paddles are available for use.

In order to insure that both paddles make good contact and thus are good electrical conductors with the human skin, it is desirable to apply a gel to the contact surfaces of the paddles. The gel may be a jelly or paste-like material capable of providing good electrical conductance. High or low-viscosity materials may be used under certain circumstances. Dry skin offers a high impedence or resistance to current flow and it is desirable to reduce the "chest impedance" so that defibrillation takes place in an efficient manner at the desired energy setting. Also, skin damage or burning may occur if a conductive material such as a gel is not used on the contact surface of the electrode.

Doctors, paramedics and others in emergency situations, when preparing for defibrillation oftentimes have to: remove a tube of gel from storage, unscrew the cap from the tube, apply the gel to the contact surface of one of the paddles, place the paddle on the ground or some other convenient spot; replace the cap on the gel tube, and then pick back up the gelled defibrillator paddle and thereafter rub the contact surface of the second defibrillator paddle against the first to insure gel distribution on both paddle surfaces, and thereafter place the paddles on the patient for defibrillation. If the patient requires a second defibrillation then the process has to be repeated and oftentimes dirt or other forms of foreign matter can come in contact with the gelled paddles if extreme precautionary measures are not taken. It is not unusual for the individual operating the defibrillation equipment, under the pressures of an emergency, to drop the tube of gel while trying to apply it to the paddle thus causing an additional waste of time as the tube is retrieved, cleaned, and then used. Also, releasing of the defibrillator paddles while applying the gel can result in the paddles being turned over or inadvertantly placed where foreign matter can easily become intermixed with the gelled surface which can cause additional problems when placed against the chest of the patient and electrically discharged.

With this background in mind and the disadvantages known, the present invention was developed and one of its objectives is to provide an apparatus and method for quickly and easily applying gel to defibrillator paddles.

Another objective of the present invention is to provide a gel dispenser which can easily be used by inexperienced defibrillation personnel.

Another objective of the present invention is to provide apparatus for dispensing gel to a defibrillator paddle which allows the user to maintain a grip at all times on the defibrillator paddle.

It is another objective of the present invention to provide a defibrillator gel dispenser which includes a easily replacable gel cartridge.

It is yet another objective of the present invention to provide a gel dispenser for defibrillator paddles which is durable in use and relatively inexpensive to manufacture.

Another objective and advantage of the present invention will be apparent to those skilled in the art in view of the detailed description below.

SUMMARY OF THE INVENTION AND DESCRIPTION OF THE PREFERRED EMBODIMENT

The invention as shown herein depicts an apparatus and method whereby gel is quickly and conveniently applied from a dispenser to the contact surface of a defibrillator paddle. The user merely slides the defibrillator paddle across an activator of the gel dispenser which is in close proximity to an outlet whereby gel under pressure flows onto the the contact surface of the defibrillator. Once the activator means is released it returns to its original position and the gel ceases to flow.

In the preferred form of the apparatus a pressurized gel reservoir is positioned beside and communicates with a valve and an outlet of the dispenser means. The valve opens by rotational movement of an activator means. A paddle guide means directs the defibrillator paddle to the activator means which opens a valve allowing gel to flow through the outlet thus providing gel to the contact surface of the paddle.

In the preferred method of the present invention the defibrillator paddle is guided from its storage location to an activator means whereby a butterfly valve is opened allowing gel to flow through the outlet and onto the contact surface of the defibrillator paddle.

DESCRIPTION OF THE DRAWING AND DETAILED DESCRIPTION OF THE INVENTION

Figures 2, 4, 5:
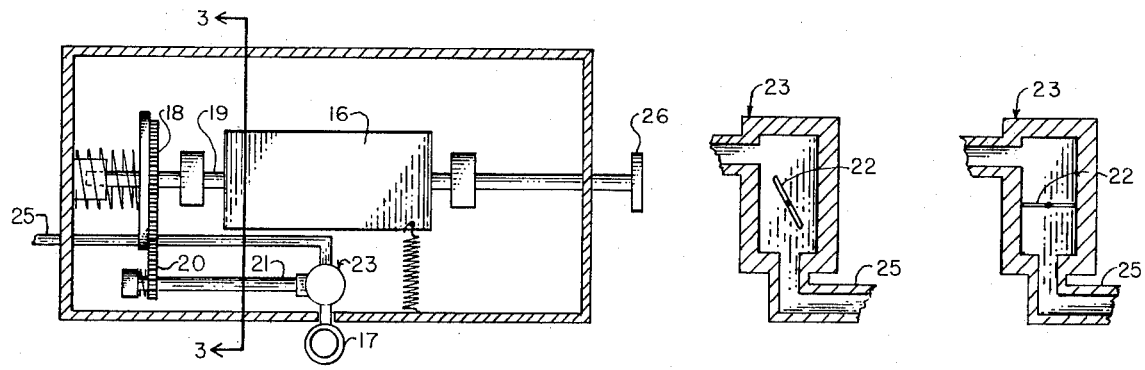
Figure 3:
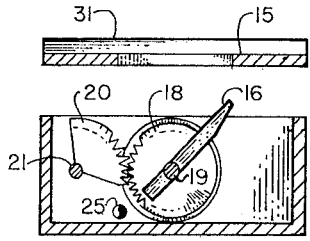
Figure 6:
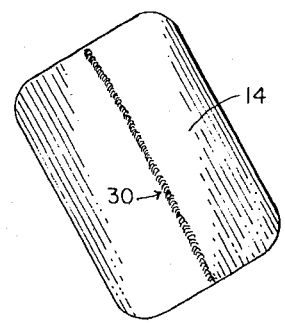

Turning now to the drawings, FIG. 1 demonstrates a perspective view of a typical defibrillator in association with the present invention;

FIG. 2 demonstrates a top view of the dispenser of the present invention;

FIG. 3 demonstrates a side-elevational view along lines 3—3 of FIG. 2;

FIG. 4 illustrates a cross-sectional view of the valve of the present invention with the butterfly valve opened;

FIG. 5 demonstrates the valve means as shown in FIG. 4 in a closed position; and FIG. 6 demonstrates the bottom of the defibrillator paddle streaked with conductive gel.

For a more detailed description of the invention, gel dispenser 10 is shown mounted on a typical defibrillator unit 11 in FIG. 1 having left-hand paddle 12 and right-hand paddle 13 positioned for storage or carrying purposes. As would be understood the underside of paddles 12 and 13 form the contact area for the skin such as contact surface 14 as shown in FIG. 6. In use, defibrillator paddle 13 is slid outward across guide means 15 having guide rails 31 where contact is made with activator means 16. Activator means 16 comprises a lever means as shown in FIG. 3 which opens valve 23 and allows gel to flow upward through outlet 17 and onto contact surface 14 of right-hand paddle 13 as it proceeds across guide means 15. Once paddle 13 clears activator means 16 then the flow of gel through outlet 17 ceases as will be explained in more detail below. Once paddle 13 has been streaked with gel 30 (as shown in FIG. 6) it can be uniformly spread across the entire contact area 14 by quickly rubbing the contact surface of paddles 12 and 13 together to provide a conductive coating of gel 30 on both contact surfaces.

Also shown in FIG. 3, activator means 16 is joined to gear means 18 by first shaft member 19. Gear means 19 meshes with quarter-gear means 20 which is affixed to second shaft member 21. Shaft member 21 in turn is joined to butterfly valve 22 shown in an open configuration in FIG. 4 and in a closed configuration in FIG. 5.

Thus, as shown in FIG. 1 gel cartridge 24 which is under pressure either by an inert gas or by a spring loaded mechanism, supplies a conductive gel through conduit 25 as shown in FIG. 2, through valve 23 as shown in FIG. 4 and upward through outlet means 17 and onto paddle 13.

In the event that the user would want to withdraw paddle 13 without dispensing the gel, then disengaging means 26 as shown in FIG. 2 could be pressed inwardly, towards activator means 16 which would disengage gear means 18 from quarter gear means 20. Disengaging means 26 could be constructed to be locked into place if desired thus, disengaging means 26 would allow paddle 13 to rotate activator means 16 while preventing the conductive gel from being streaked onto paddle contact surface 14 if desired. Resilient member 27 returns gear means 18 to its normal operating position and into mesh with quarter gear means 20 when disengaging means 26 is released.

Other embodiments of the apparatus can be made other than those shown in the figures presented herewith and the examples and illustrations shown are for illustrative purposes and are not intended to limit the scope of the invention.

I claim:

1. Apparatus for dispensing gel to a defibrillator paddle comprising: a gel reservoir, a valve, said valve communicating with said reservoir, activator means, said activator means for opening said valve, defibrillator paddle guide means, said guide means for directing the paddle to said activator means, an outlet, said outlet proximate said activator means, said outlet communicating with said gel reservoir whereby activating said activator means allows gel to flow through said valve and onto the defibrillator paddle.

2. Apparatus as claimed in claim 1 wherein said activator means comprises lever means.

3. Apparatus as claimed in claim 1 wherein said valve comprises a butterfly valve.

4. Wherein apparatus as claimed in claim 1 wherein said gel reservoir is pressurized.

5. Apparatus as claimed in claim 1 wherein a portion of said activator means extends above said guide means.

6. A method for applying gel to a defibrillator paddle comprising: guiding the paddle onto an activator means, activating said activator means with the paddle, opening a valve and allowing gel to flow through said valve to the paddle.

7. A method as claimed in claim 6 wherein the step of guiding the paddle comprises guiding the paddle over a guide means.

8. A method as claimed in claim 6 wherein the step of activating the activating means comprises rotating the activating means.

9. A method as claimed in claim 6 wherein the step of allowing gel to flow through said valve comprises streaking gel onto the paddle contact surface.

* * * * *